United States Patent [19]

Rottmaier et al.

[11] 4,433,144
[45] Feb. 21, 1984

[54] GLYCOLURIL SALTS AND A PROCESS FOR THE PREPARATION THEREOF

[75] Inventors: Ludwig Rottmaier, Odenthal; Rudolf Merten, Leverkusen, both of Fed. Rep. of Germany

[73] Assignee: Bayer Aktiengesellschaft, Leverkusen, Fed. Rep. of Germany

[21] Appl. No.: 378,894

[22] Filed: May 17, 1982

Related U.S. Application Data

[63] Continuation-in-part of Ser. No. 356,022, Mar. 8, 1982, abandoned.

[30] Foreign Application Priority Data

Mar. 12, 1981 [DE] Fed. Rep. of Germany ....... 3109478

[51] Int. Cl.³ .......................................... C07D 487/04
[52] U.S. Cl. .................................... 544/198; 544/207
[58] Field of Search ............................. 544/198, 207

[56] References Cited
FOREIGN PATENT DOCUMENTS 2229439 12/1972 Fed. Rep. of Germany .

OTHER PUBLICATIONS

Smolin et al., "s-Triazines and Derivatives," Interscience Publ., New York, (1959), pp. 326–327.
Chemical Abstracts, vol. 92, No. 11, 94365x, (3/17/80).
Bielsteins Handbuch der Organischen Chemie, vol. 26, pp. 441–443, (1937).

Primary Examiner—John M. Ford
Attorney, Agent, or Firm—Connolly and Hutz

[57] ABSTRACT

This invention is directed to glycoluril-triazine salts of the formula:

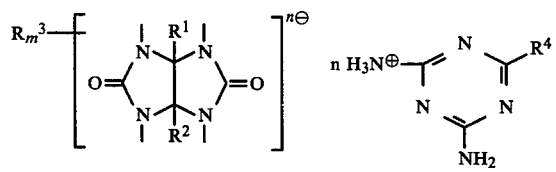

wherein the R's are hydrogen and hydrocarbon radicals, n is 1 to 4, and m is 4−n. These materials are suitable for modifying polymers, such as polyurethanes and flameproofing polyamides.

8 Claims, No Drawings

GLYCOLURIL SALTS AND A PROCESS FOR THE PREPARATION THEREOF

This is a continuation-in-part of Ser. No. 356,022, filed Mar. 8, 1982, now abandoned.

This invention relates to salts of aminotriazines and glycolurils of the following general formula (I)

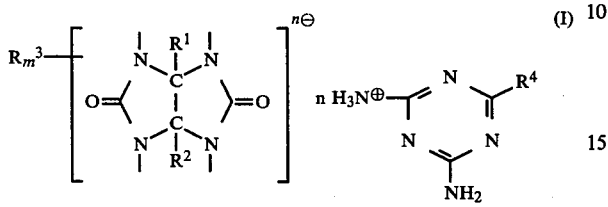

wherein:

$R^1$ and $R^2$ may be the same or different and represent hydrogen, an aliphatic $C_1-C_{20}$, or an aromatic $C_6-C_{10}$ radical, $R^3$ represents hydrogen, an aliphatic $C_1-C_{20}$, a cycloaliphatic $C_4-C_{15}$, an araliphatic $C_7-C_{15}$ or an aromatic $C_6-C_{15}$ radical, $R^4$ represents hydrogen, an amino group, an aliphatic $C_1-C_{20}$, cycloaliphatic $C_4-C_{17}$, araliphatic $C_7-C_{17}$ or aromatic $C_6-C_{15}$ radical, n represents an integer from 1 to 4, and m represents $4-n$, and the radicals $R^1$, $R^2$, $R^3$ and $R^4$ may be substituted with hydroxyl, halogen atoms (Cl, Br, F) or alkoxy groups having from 1 to 4 carbon atoms.

$R^1$ and $R^2$ are preferably unsubstituted and preferably represent hydrogen, a $C_1-C_{10}$ alkyl radical or a phenyl radical, in particular hydrogen, methyl, ethyl, propyl or butyl. $R^1$ and $R^2$ most preferably represent hydrogen or a methyl group.

$R^3$ is preferably unsubstituted and preferably represents hydrogen, an aliphatic $C_1-C_{10}$, a cycloaliphatic $C_4-C_{10}$, an araliphatic $C_7-C_{10}$ or an aromatic $C_6-C_{10}$ radical, in particular hydrogen or a methyl, ethyl, propyl, butyl, cyclohexyl, benzyl or phenyl radical. $R^3$ most preferably represents hydrogen or a methyl group.

The radical $R^4$ is preferably unsubstituted and preferably represents hydrogen, an amino group, an aliphatic $C_1-C_{10}$, a cycloaliphatic $C_4-C_{10}$, an araliphatic $C_7-C_{10}$ or an aromatic $C_6-C_{10}$ radical, in particular hydrogen, an amino group, an aliphatic $C_1-C_6$, cycloaliphatic $C_4-C_6$, benzyl or phenyl radical. $R^4$ most preferably represents the amino group.

The starting glycolurils which are required for the preparation of the salts according to the present invention may be prepared according to known processes from α, β-diketo compounds and ureas, optionally in the presence of acidic catalysts. The glycolurils may be prepared, for example, analogously to the instructions described in Liebigs Annalen 189, (1877) P. 157.

The starting triazines which are required for the preparation of the salts according to the present invention may be prepared in accordance with known processes, for example, from nitriles and dicyanodiamide in polar organic solvents such as, for example, dimethylsulphoxide, as in Bulletin of the Chemical Society, Japan 38, No. 11 (1965) 1820.

The salts according to the present invention of the general formula (1) are obtained by reacting glycolurils of the following general formula (II):

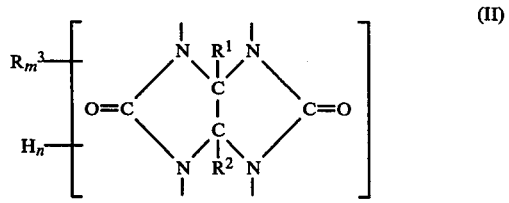

wherein $R^1$, $R^2$, $R^3$, m and n are as defined above, with n mols of triazine of the following general formula (III):

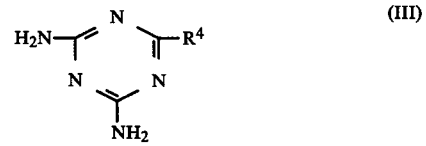

wherein $R^4$ is as defined above, optionally in a solvent.

The reaction of the glycolurils with the triazines is usually carried out using equivalent quantities, preferably each of the NH groups of the glycoluril may be reacted with one triazine. Consequently, glycolurils of the general formula (II) wherein $R^3$ represents hydrogen, may react with 4 mols of triazine. However, it is also possible to prepare compounds with, for example, 2 mols of triazine, so that still NH groups are contained in the salts according to the invention of the general formula (I).

The reaction between the glycolurils and the triazines may be carried out in the melt or in solvents. However, the reaction is preferably carried out in solvents.

Solvents which do not react with the reaction components, in particular polar solvents, may be used as the solvents.

However, the reaction between the glycolurils and the triazines is advantageously carried out in an aqueous medium and/or in water-miscible solvents. Examples of these water-miscible solvents are as follows: alcohols, such as methanol, ethanol, isopropanol, glycolmonomethylether and glycol, cyclic ethers such as tetrahydrofuran and dioxane, alkyl amides and dialkyl amides such as dimethylformamide, dimethylacetamide and N-methylpyrrolidone. Of course, mixtures of these solvents or mixtures with water may also be used. After the reaction is finished, and possibly to improve the working up of the resulting glycoluril salts, other solvents may also be added, for example, aliphatic or aromatic hydrocarbons (ligroin, cyclohexane, toluene or xylene), chlorinated hydrocarbons (methylene chloride, chloroform or chlorobenzene) and esters (acetic acid ethyl ester or butyl ester).

Water in particular is used as a solvent during the reaction between the glycolurils and the triazines, because the required compound frequently crystallizes out of the aqueous solution in practically pure form.

The salt formation between the glycolurils and the triazines is carried out at from 0° to 180° C., preferably from 30° to 130° C., optionally under elevated pressure.

The reaction time generally range between a few minutes and several hours, but they may be longer in special cases. Shorter reaction times are achieved by a corresponding selection of the reaction conditions, e.g. pressure.

The glycoluril-triazine salts of the general formula (I) are suitable for modifying polymeric substances. They may be used for the preparation and modification of polyurethanes or for flameproofing thermoplastic polyamides.

Glycolurils or reaction products of the glycolurils are added to the polyamide resin in a quantity of from 0.1 to 20% by weight, preferably of from 0.5 to 15% by weight. When using glycolurils, a quantity of from 0.1 to 5% by weight, preferably from 0.5 to 3% by weight is sufficient for flame-proofing. However, the reaction products of the glycolurils are added to the polyamide resin in a quantity of from 0.1 to 20% by weight, preferably from 1 to 20, most preferably from 3 to 15% by weight. Of course, mixtures of glycolurils and the reaction products of glycolurils may also be used. It is also possible to add other flameproofing agents, for example, halogen compounds or red phosphorus, to the moulding composition.

The polyamide moulding compositions according to the present invention may contain up to 60% by weight of reinforcing materials and fillers. The following are used reinforcing materials and fillers:

glass fibres, carbon fibres, asbestos fibres, glass beads, talcum, mica, wollastonite, microvit, chalk, silicon dioxide, graphite, gypsum and other conventional additives, such as pigments and dyes, e.g. cadmium sulphide, phthalocyanines and titanium dioxide.

Copper compounds or a mixture of a copper compound and an alkali metal halide may be added in quantities of from 0.001 to 1% by weight as additional flameproofing agents to the polyamide moulding compsitions according to the present invention.

Suitable copper compounds include organic and inorganic copper salts. The following are mentioned as examples: copper(I)chloride, copper(II)sulphate, copper(I)iodide, copper(II)phosphate, copper(II)acetate, copper(II)stearate, copper(II)benzoate and copper-chelate compounds. Suitable alkali metal halides include potassium iodide, potassium bromide, sodium chloride and sodium bromide.

Aromatic and/or higher aliphatic carboxylic acids and the alkali metal or alkaline-earth metal salts thereof, e.g. sodium stearate, calcium stearate, isophthalic acid and terephthalic acid, may be worked into the polyamide resin compositions according to the invention as aids and additives in quantities of from 0.1 to 1% by weight.

It is also possible to add any known antistatic agents such as conductive carbon black or quaternary ammonium salts.

The additives may be added to the polyamide resin according to the most varied known processes, preferably before moulding. The simplest process comprises admixing the additives dry with the polyamide resin. The dry-mixed material may then be melted and extruded for the production of granulates. The additives may also be admixed with the plasticised polyamide resin composition in the extruder using known metering apparatus. It is also possible initially to produce masterbatch granulates by admixing large quantities of the additives with the polyamide resin and then to mix these master-batch granulates with the polyamide resin.

The mouldings may be produced by moulding the composition or the granulates using various moulding machines, in particular injection moulding machines or extruding machines, pressing machines or the like. The additives may also be worked in using the moulding machine.

Usually the aditives are dosed to the polyamide at the processing temperature which is usually at least 10° C., but not more that 30° C., above the softening temperature of the polyamide. For example, in case of polyamide-6,6, the processing temperature is below 270° C., whereas in the case of polyamide-6, temperatures of below 250° C. are sufficient.

The polyamide resin compositions according to the present invention do not only exhibit an outstanding flame resistance, outstanding mechanical properties and an outstanding workability, but can be produced in light colours.

In the following Examples, percentages represent % by weight and parts represent parts by weight.

EXAMPLE 1

3.55 kg of glycoluril are added to a mixture of 12.6 kg of melamine and 75 kg of water at 95° C. with stirring. In order to complete the reaction, the mixture is stirred for 3 hours under slight reflux. At 80° C., the resulting deposit is filtered with suction, washed with hot water and dried at 100° C. in a circulating air drying chamber to a constant weight. 13.1 kg of a salt formed from 1 mol of glycoluril and 4 mols of melamine are obtained, the structure of which is proved by IR spectrum and elemental analysis.

$C_{16}H_{30}N_{28}O_2$ (646.6). Calculated: C=29.72%, H=4.68%, N=60.66%. Found: C=29.5%, H=4.7%, N=60.4%.

EXAMPLE 2

(a) 7.1 kg of glycoluril are added to a mixture of 12.6 kg of melamine and 75 kg of water at 95° C. In order to complete the reaction, the mixture is stirred for 3 hours at 95° C. and filtered hot with suction, washed with water and dried at 100° C. in a circulating air drying chamber. 15.75 kg of a salt formed from 1 mol of glycoluril and 2 mols of melamine are obtained, the structure of which confirmed by IR spectrum and elemental analysis.

$C_{10}H_{18}N_{16}O_2$ (394.4). Calculated: C=30.45%, H=4.60%, N=56.83%. Found: C=30.4%, H=4.7%, N=56.9%.

(b) 92.5% by weight of polyamide-6 having a relative viscosity (measured on a solution of 1 g of polyamide in 100 ml of m-cresol at 25° C.) of 2.9 are mixed with 7.5% by weight of the melamine-glycoluril salt prepared according to a) in the melt in a double shaft extruder under the conditions conventional for polyamide-6. The strand which is drawn off is cooled, granulated and dried. The granulated material is then injected to form test bodies according to ASTM of ¼, ⅛, and 1/16 of an inch on an injection moulding machine A 270 manufactured by Arburg.

These test bodies are stored for 7 days in a drying chamber at 70° C. and are then subjected to the "Vertical Burning Test for Classifying Materials" according to Underwriter's Laboratories (UL) Subject 94. A classification of VO was obtained for all the test bodies, whereas the result of the test for polyamide-6 without the melamine-glycoluril salt was V2.

EXAMPLE 3

17 g of 3a, 6a-dimethyl-glycoluril are added to a mixture of 50.4 g of melamine and 300 g of water with stirring at 95° C. and are stirred for 3 hours at this temperature. The crystalline deposit is filtered hot with suction, washed with water and dried under vacuum at 30 mbar at 80° C. 58.2 g of a salt with 4 mols of melamine are obtained, the structure of which is confirmed by IR spectrum and elemental analysis.

$C_{18}H_{34}N_{28}O_2$ (674.7). Calculated: C=32.04%, H=5.08%, N=58.13%. Found: C=32.2%, H=5.2%, N=58.0%.

EXAMPLE 4

50.4 of melamine and 34 g of 3a,6a-dimethylglycoluril in 300 g of water are reacted analogously to Example 3. After drying, 73.2 g of a salt with 2 mols of melamine are obtained, the structure of which is confirmed by IR spectrum and elemental analysis.

$C_{12}H_{22}N_{16}O_2$ (422.4). Calculated: C=34.12%, H=5.25%, N=53.06%. Found: C=34.0%, H=5.3%, N=53.2%.

EXAMPLE 5

50.4 g of melamine and 34 g of 1,4-dimethylglycoluril in 300 g of water are reacted analogously to Example 3. After drying, 72.4 g of a salt with 2 mols of melamine are obtained, the structure of which is confirmed by IR spectrum and elemental analysis.

$C_{12}H_{22}N_{16}O_2$ (422.4). Calculated: C=34.12%, H=5.25%, N=53.06%. Found: C=33.9%, H=5.1%, N=53.3%.

We claim:

1. A glycoluril-triazine salt of the formula (I):

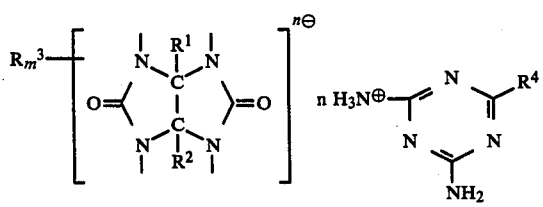

wherein:

$R_1$ and $R^2$ each independently represent hydrogen, an aliphatic $C_1-C_{20}$ or an aromatic $C_6-C_{10}$ radical, $R_3$ represents hydrogen, an aliphatic $C_1-C_{20}$, a cycloaliphatic $C_4-C_{15}$, an aralphatic $C_7-C_{15}$ or an aromatic $C_6-C_{15}$ radical, $R^4$ represents hydrogen, an amino group, an aliphatic $C_1-C_{20}$, a cycloaliphatic $C_4-C_{17}$, an aralphatic $C_7-C_{17}$ or an aromatic $C_6-C_{15}$ radical, n represents an integer from 1 to 4, m represents 4−n, and the radicals $R^1$, $R^2$, $R^3$ and $R^4$ may each independently be substituted by hydroxyl, halogen or a $C_1-C_4$ alkoxy group.

2. A glycoluril-triazine salt as claimed in claim 1, wherein $R^4$ represents an amino group.

3. A salt as claimed in claim 1, wherein $R^1$ and $R^2$ represent hydrogen, a $C_1-C_{10}$ aklyl radical or a phenyl radical.

4. A salt as claimed in claim 3, wherein $R^1$ and $R^2$ represent hydrogen or a methyl group.

5. A salt as claimed in claim 1, wherein $R^3$ represents hydrogen, an aliphatic $C_1-C_{10}$, a cycloaliphatic $C_4-C_{10}$, an aralphatic $C_7-C_{10}$ or an aromatic $C_6-C_{10}$ radical.

6. A salt as claimed in claim 5, wherein $R^3$ represents hydrogen or a methyl group.

7. A process for the preparation of a glycoluril-triazine salt as claimed in claim 1, wherein a glycoluril of the formula (II):

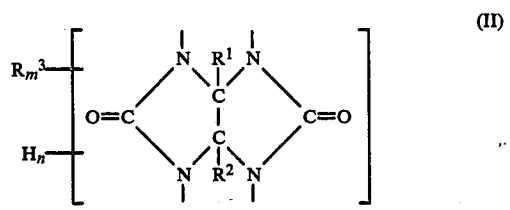

wherein $R^1$, $R^2$, $R^3$, m and n are as defined in claim 1, is reacted with a triazine of the following general formula (III):

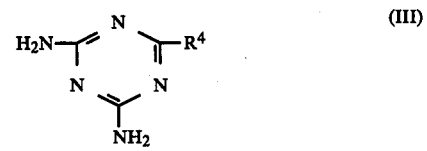

wherein $R^4$ is as defined in claim 1, in water and/or in an organic solvent at a temperature of from 0° to 180° C.

8. A process as claimed in claim 7, wherein n mols of triazine are used per mol glycoluril.

* * * * *